United States Patent
Takenaka et al.

(10) Patent No.: US 9,462,989 B2
(45) Date of Patent: Oct. 11, 2016

(54) IMAGING APPARATUS AND IMAGING SYSTEM

(71) Applicant: CANON KABUSHIKI KAISHA, Tokyo (JP)

(72) Inventors: Katsuro Takenaka, Honjo (JP); Toshio Kameshima, Kumagaya (JP); Tomoyuki Yagi, Honjo (JP); Sho Sato, Saitama (JP); Atsushi Iwashita, Saitama (JP); Eriko Sato, Tokyo (JP); Hideyuki Okada, Honjo (JP); Takuya Ryu, Kokubunji (JP)

(73) Assignee: Canon Kabushiki Kaisha, Tokyo (JP)

( * ) Notice: Subject to any disclaimer, the term of this patent is extended or adjusted under 35 U.S.C. 154(b) by 115 days.

(21) Appl. No.: 14/138,918

(22) Filed: Dec. 23, 2013

(65) Prior Publication Data

US 2014/0185764 A1    Jul. 3, 2014

(30) Foreign Application Priority Data

Dec. 28, 2012 (JP) ................................. 2012-288451

(51) Int. Cl.
*A61B 6/00* (2006.01)
*H05G 1/38* (2006.01)
*H04N 5/32* (2006.01)

(52) U.S. Cl.
CPC ............. *A61B 6/542* (2013.01); *A61B 6/42* (2013.01); *H04N 5/32* (2013.01); *H05G 1/38* (2013.01)

(58) Field of Classification Search
CPC ........... A61B 6/542; H05G 1/38; H05G 1/42
See application file for complete search history.

(56) References Cited

U.S. PATENT DOCUMENTS

| | | | |
|---|---|---|---|
| 7,408,167 B2 | 8/2008 | Kameshima et al. | |
| 7,442,939 B2 | 10/2008 | Yagi et al. | |
| 7,514,690 B2 | 4/2009 | Endo et al. | |
| 7,573,041 B2 | 8/2009 | Kameshima et al. | |
| 7,791,034 B2 | 9/2010 | Kameshima et al. | |
| 7,872,218 B2 | 1/2011 | Endo et al. | |
| 2003/0213914 A1* | 11/2003 | Kobayashi ............ | G01T 1/2018 250/370.09 |
| 2004/0149920 A1* | 8/2004 | Ishii ...................... | G01T 1/2928 250/370.08 |

FOREIGN PATENT DOCUMENTS

| | | |
|---|---|---|
| JP | 11-188021 A | 7/1999 |
| JP | 2004-73256 A | 3/2004 |

* cited by examiner

*Primary Examiner* — Glen Kao
(74) *Attorney, Agent, or Firm* — Fitzpatrick, Cella, Harper & Scinto

(57) ABSTRACT

An imaging apparatus has an AEC function that can prevent irregularities in photographed images, without being increased in size. The imaging apparatus comprises a plurality of pixels arranged in a matrix shape, each of the plurality of pixels including a conversion element for converting radiation or light into an electric charge, a plurality of lines that are connected to the plurality of pixel units and that extend in different directions to each other, a current monitor circuit that monitors currents flowing in the plurality of lines, and an arithmetic unit that calculates a two-dimensional distribution by performing back-projection processing with respect to the currents flowing in the plurality of lines monitored by the current monitor circuit.

7 Claims, 13 Drawing Sheets

| VS1 | VS2 | VS3 | VS4 | VS5 | VS6 | VS7 | VS8 |
|---|---|---|---|---|---|---|---|
| 0 | 0 | 1 | 3 | 26 | 3 | 1 | 0 |

| | | | | | | |
|---|---|---|---|---|---|---|
| 0 | 0 | 1 | 3 | 26 | 3 | 1 | 0 |
| 0 | 0 | 1 | 3 | 26 | 3 | 1 | 0 |
| 0 | 0 | 1 | 3 | 26 | 3 | 1 | 0 |
| 0 | 0 | 1 | 3 | 26 | 3 | 1 | 0 |
| 0 | 0 | 1 | 3 | 26 | 3 | 1 | 0 |
| 0 | 0 | 1 | 3 | 26 | 3 | 1 | 0 |
| 0 | 0 | 1 | 3 | 26 | 3 | 1 | 0 |
| 0 | 0 | 1 | 3 | 26 | 3 | 1 | 0 |

| | |
|---|---|
| VG1 | 0 |
| VG2 | 1 |
| VG3 | 18 |
| VG4 | 1 |
| VG5 | 1 |
| VG6 | 18 |
| VG7 | 1 |
| VG8 | 0 |

| | | | | | | |
|---|---|---|---|---|---|---|
| 0 | 0 | 1 | 3 | 26 | 3 | 1 | 0 |
| 1 | 1 | 2 | 4 | 27 | 4 | 2 | 1 |
| 18 | 18 | 19 | 21 | 44 | 21 | 19 | 18 |
| 1 | 1 | 2 | 4 | 27 | 4 | 2 | 1 |
| 1 | 1 | 2 | 4 | 27 | 4 | 2 | 1 |
| 18 | 18 | 19 | 21 | 44 | 21 | 19 | 18 |
| 1 | 1 | 2 | 4 | 27 | 4 | 2 | 1 |
| 0 | 0 | 1 | 3 | 26 | 3 | 1 | 0 |

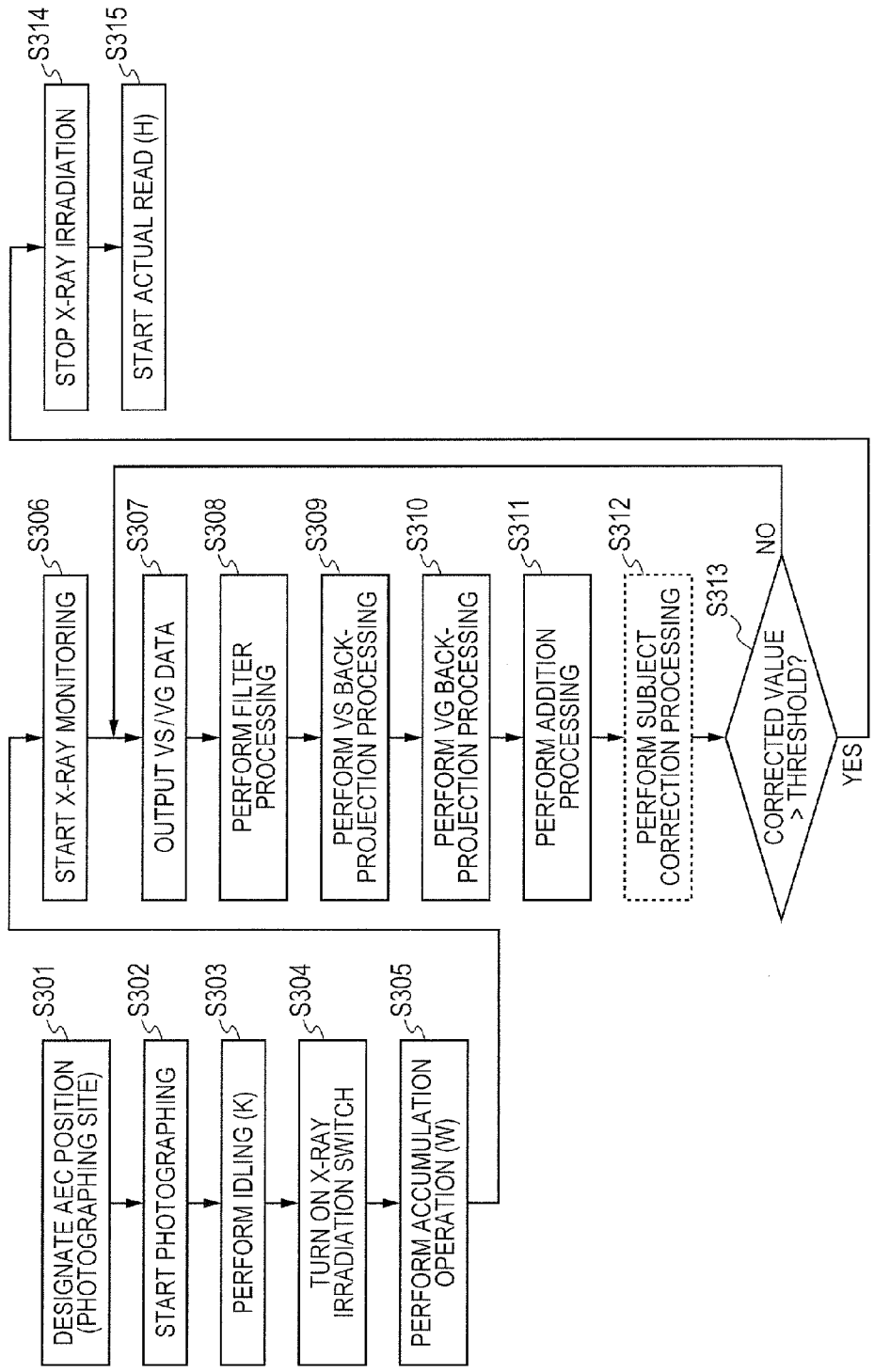

AFTER SUBJECT CORRECTION

| | 1 COLUMN | 2 COLUMN | 3 COLUMN | 4 COLUMN | 5 COLUMN | 6 COLUMN | 7 COLUMN | 8 COLUMN |
|---|---|---|---|---|---|---|---|---|
| 1 ROW | 236 | 184 | 171 | 173 | 185 | 202 | 208 | 287 |
| 2 ROW | 234 | 175 | 220 | 182 | 191 | 286 | 209 | 250 |
| 3 ROW | 241 | 194 | 253 | 191 | 222 | 332 | 232 | 278 |
| 4 ROW | 258 | 235 | 278 | 187 | 223 | 360 | 282 | 315 |
| 5 ROW | 2690 | 277 | 339 | 176 | 191 | 357 | 280 | 2397 |
| 6 ROW | 2670 | 292 | 291 | 147 | 155 | 306 | 261 | 2375 |
| 7 ROW | 2642 | 194 | 149 | 129 | 131 | 155 | 199 | 2346 |
| 8 ROW | 2601 | 156 | 134 | 128 | 128 | 138 | 183 | 2310 |

=

SUBJECT CORRECTION COEFFICIENTS

| | 1 COLUMN | 2 COLUMN | 3 COLUMN | 4 COLUMN | 5 COLUMN | 6 COLUMN | 7 COLUMN | 8 COLUMN |
|---|---|---|---|---|---|---|---|---|
| 1 ROW | 0.24 | 0.59 | 0.61 | 0.68 | 0.70 | 0.65 | 0.64 | 0.30 |
| 2 ROW | 0.23 | 0.56 | 0.75 | 0.71 | 0.72 | 0.92 | 0.64 | 0.26 |
| 3 ROW | 0.24 | 0.60 | 0.83 | 0.71 | 0.80 | 1.03 | 0.68 | 0.29 |
| 4 ROW | 0.25 | 0.70 | 0.88 | 0.67 | 0.78 | 1.08 | 0.81 | 0.32 |
| 5 ROW | 2.11 | 0.47 | 0.59 | 0.33 | 0.35 | 0.61 | 0.46 | 1.95 |
| 6 ROW | 2.10 | 0.50 | 0.52 | 0.28 | 0.29 | 0.53 | 0.44 | 1.95 |
| 7 ROW | 2.10 | 0.34 | 0.27 | 0.25 | 0.25 | 0.27 | 0.34 | 1.94 |
| 8 ROW | 2.06 | 0.27 | 0.24 | 0.25 | 0.24 | 0.24 | 0.31 | 1.90 |

×

AFTER ADDITION PROCESSING

| | 1 COLUMN | 2 COLUMN | 3 COLUMN | 4 COLUMN | 5 COLUMN | 6 COLUMN | 7 COLUMN | 8 COLUMN |
|---|---|---|---|---|---|---|---|---|
| 1 ROW | 999 | 311 | 292 | 255 | 263 | 311 | 327 | 948 |
| 2 ROW | 1001 | 313 | 294 | 257 | 265 | 313 | 329 | 950 |
| 3 ROW | 1012 | 324 | 305 | 268 | 276 | 324 | 339 | 961 |
| 4 ROW | 1021 | 333 | 314 | 277 | 285 | 333 | 349 | 970 |
| 5 ROW | 1277 | 589 | 570 | 533 | 541 | 589 | 605 | 1226 |
| 6 ROW | 1271 | 583 | 564 | 526 | 534 | 582 | 598 | 1220 |
| 7 ROW | 1257 | 569 | 550 | 513 | 521 | 569 | 585 | 1206 |
| 8 ROW | 1265 | 577 | 558 | 520 | 528 | 576 | 592 | 1214 |

IMAGING APPARATUS AND IMAGING SYSTEM

BACKGROUND OF THE INVENTION

1. Field of the Invention

The present invention relates to an imaging apparatus and an imaging system.

2. Description of the Related Art

In recent years, radiation imaging apparatuses including a flat panel detector (hereinafter abbreviated as "FPD") formed of a semiconductor material have started to be put to practical use as photographing apparatuses that are used for medical diagnostic imaging or nondestructive inspection using X-rays. The radiation imaging apparatuses that use an FPD are capable of digital photographing in which radiation such as X-rays that were transmitted through a subject such as a patient are converted into analog electrical signals at the FPD, and the analog electrical signals are subjected to analog-to-digital conversion to acquire digital image signals. The FPDs that are used in such radiation imaging apparatuses are broadly divided into direct-conversion type FPDs and indirect-conversion type FPDs. A direct-conversion type radiation imaging apparatus includes an FPD in which a plurality of pixels that include a conversion element made using a semiconductor material, such as a-Se, that is capable of converting radiation directly into an electric charge are arranged in a two-dimensional shape. An indirect-conversion type radiation imaging apparatus includes an FPD in which a plurality of pixels that include a conversion element having a wavelength converter such as a phosphor that can convert radiation into light and a photoelectric conversion element made using a semiconductor material such as a-Si that can convert light into an electric charge are arranged in a two-dimensional shape. Such radiation imaging apparatuses that include an FPD are used, for example, in medical diagnostic imaging as digital imaging apparatuses for still image photographing like general photographing or moving image photographing such as fluoroscopy. In X-ray photographing, AEC (automatic exposure control) is used so that the amount of X-rays transmitted through a subject is within a photographing range that can be detected by a radiation imaging apparatus and also to suppress to the minimum the amount of X-ray exposure of a subject.

SUMMARY OF THE INVENTION

In Japanese Patent Application Laid-Open No. H11-188021, an AEC sensor is provided separately to a detector for imaging a subject, and is disposed on the rear face of the radiation imaging apparatus and controls an X-ray generating apparatus. Consequently, in the case of a portable radiation imaging apparatus, there is the problem that the radiation imaging apparatus becomes thicker and is difficult to carry. Further, in Japanese Patent Application Laid-Open No. 2004-73256, AEC sensors are formed between pixels for imaging a subject. When the AEC sensors are disposed between pixels, there is the problem that irregularities arise in photographed images because the pixel layout is uneven in regions where the AEC sensors are disposed.

An object of the present invention is to provide an imaging apparatus and an imaging system that, without being increased in size, have an AEC function that can prevent irregularities in photographed images.

In order to achieve the object, the present invention provides an imaging apparatus comprising a plurality of pixels arranged in a matrix shape, each of the plurality of pixels including a conversion element for converting radiation or light into an electric charge, a plurality of lines that are connected to the plurality of pixels and that extend in different directions to each other, a current monitor circuit that monitors currents flowing in the plurality of lines, and an arithmetic unit that calculates a two-dimensional distribution by performing back-projection processing with respect to the currents flowing in the plurality of lines monitored by the current monitor circuit.

According to the present invention, an imaging apparatus can be provided that, without being increased in size, has an AEC function that can prevent irregularities in photographed images.

Further features of the present invention will become apparent from the following description of exemplary embodiments with reference to the attached drawings.

BRIEF DESCRIPTION OF THE DRAWINGS

FIG. 5 is a flowchart of operations of the imaging system according to the first embodiment.

FIGS. 7A, 7B and 7C are views illustrating a processing method of the imaging system according to the first embodiment.

FIG. 8 is a view illustrating a processing method of the imaging system according to the first embodiment.

DESCRIPTION OF THE EMBODIMENTS

Preferred embodiments of the present invention will now be described in detail in accordance with the accompanying drawings.

First Embodiment

Figure 1:
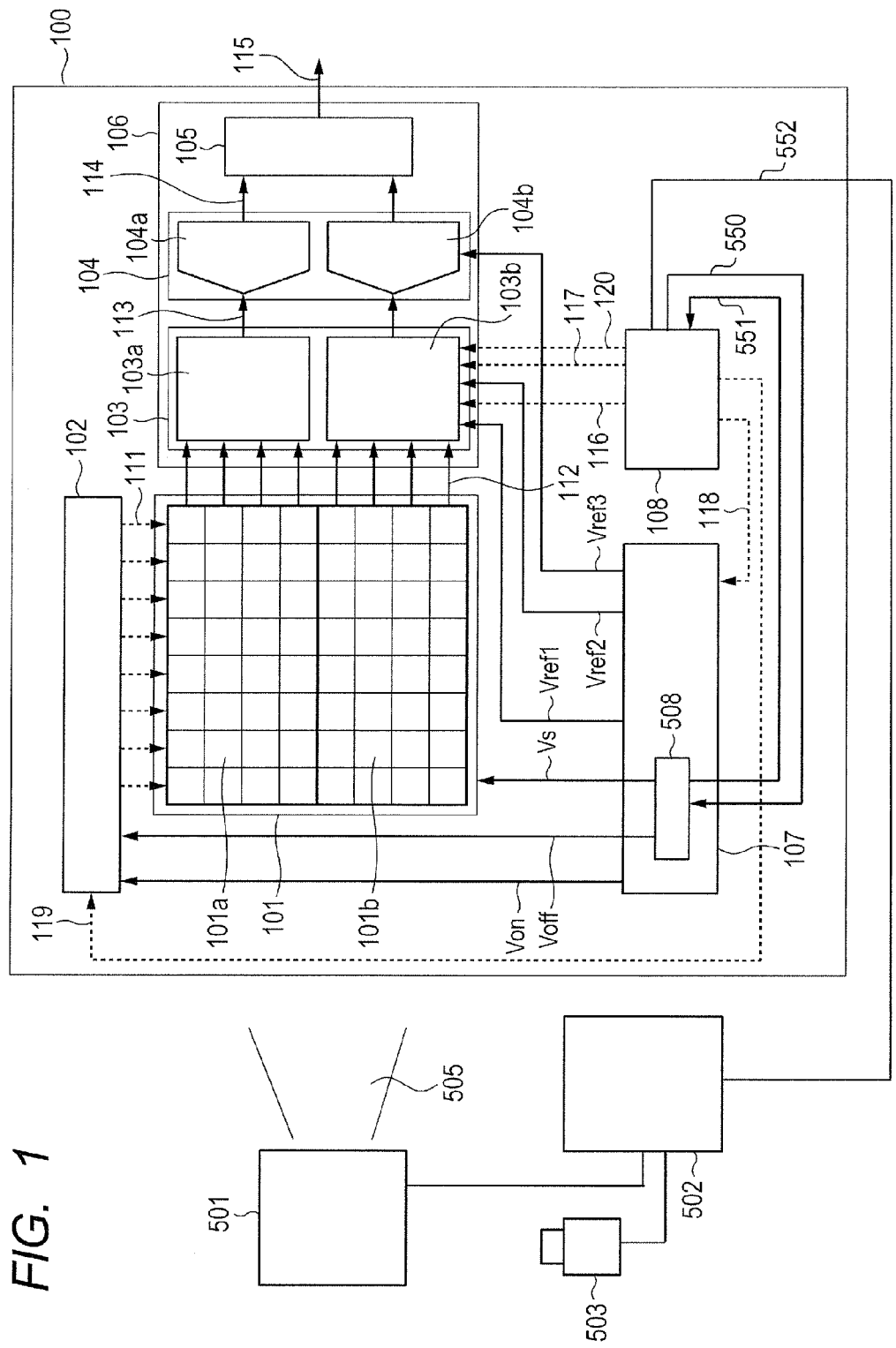
FIG. 1 is a view of an imaging system according to a first embodiment.

FIG. 1 is a block diagram of an imaging system including an imaging apparatus and an X-ray generating apparatus according to a first embodiment of the present invention. The imaging system can be used for diagnosis for medical treatment or for nondestructive inspections for industrial use. An imaging apparatus 100 includes a detection unit 101 that includes a plurality of pixels for converting radiation or light into an analog electrical signal that are arranged in a matrix shape, and a drive circuit 102 that drives the detection unit 101 to output an analog electrical signal from the detection unit 101. The term "radiation" includes electromagnetic waves such as X-rays and γ-rays, and α-rays and β-rays. According to the present embodiment, to simplify the description it is assumed that the detection unit 101 includes pixels arranged to form 8 rows and 8 columns and is divided into is a first pixel group 101a and a second pixel group 101b that each includes four pixel columns. An analog electrical signal 112 that is output from the first pixel group 101a is read by a corresponding first read circuit 103a. An analog electrical signal 113 from the first read circuit 103a is converted to a digital signal 114 by a corresponding first A/D converter 104a. Similarly, the analog electrical signal 112 from the second pixel group 101b is read by a corresponding second read circuit 103b. An analog electrical signal from the second read circuit 103b is converted to a digital signal by a corresponding second A/D converter 104b. The digital signals from the first and second A/D converters 104a and 104b are subjected to simple digital signal processing, such as digital multiplex processing or offset correction, by a digital signal processing unit 105, and a resulting digital image signal 115 is output.

A signal processing unit 106 has a read circuit unit 103 that includes the first and second read circuits 103a and 103b, an A/D converter unit 104 that includes the first and second A/D converters 104a and 104b, and the digital signal processing unit 105. The imaging apparatus 100 further includes a power supply unit 107 that applies a bias to the signal processing unit 106. The power supply unit 107 outputs a first reference voltage Vref1 and a second reference voltage Vref2 to the read circuit unit 103, and outputs a third reference voltage Vref3 to the A/D converter unit 104. The power supply unit 107 also supplies an on-bias voltage Von for turning on switching elements inside the pixels as well as an off-bias voltage Voff for turning off the switching elements to the drive circuit 102. In addition, the power supply unit 107 supplies a sensor bias Vs that is applied to photoelectric conversion elements of the detection unit 101. The power supply unit 107 includes an AEC monitor unit 508 that has an AEC function by monitoring a current that flows in the sensor bias Vs and the off-bias voltage Voff. The imaging apparatus 100 further includes a control unit 108 for controlling at least one of the signal processing unit 106 and the power supply unit 107. The control unit 108 supplies a drive control signal 119 to the drive circuit 102. The drive circuit 102 supplies a drive signal 111 to the detection unit 101 based on the drive control signal 119. The control unit 108 supplies an operation control signal 118 to the power supply unit 107, and the power supply unit 107 controls a bias that is supplied to the detection unit 101, the drive circuit 102 and the read circuit unit 103. The control unit 108 also supplies signals 116, 117 and 120 for controlling the read circuit unit 103.

Reference numeral 501 denotes an X-ray generating apparatus (radiation generating apparatus), reference numeral 502 denotes an X-ray control apparatus for controlling the X-ray generating apparatus 501, and reference numeral 503 denotes an exposure button that a user uses to perform X-ray irradiation. Reference numeral 552 denotes a communication signal for communication between the imaging apparatus 100 and the X-ray control apparatus 502. Reference numeral 505 denotes X-ray beams. When the user presses the exposure button 503, the X-ray control apparatus 502 outputs a confirmation signal indicating whether or not irradiation of X-rays is possible to the imaging apparatus 100 through the communication signal 552. When an enabling signal is input from the imaging apparatus 100, the X-ray generating apparatus 501 is caused to start irradiation of the X-ray beams 505. After X-ray irradiation starts, the AEC monitor unit 508 monitors the amount of X-ray irradiation, and if the amount of X-ray irradiation becomes equal to or greater than a certain amount the imaging apparatus 100 outputs a stop signal to the X-ray control apparatus 502, and the X-ray control apparatus 502 stops the irradiation of the X-ray beams 505 by the X-ray generating apparatus 501.

Figure 2:
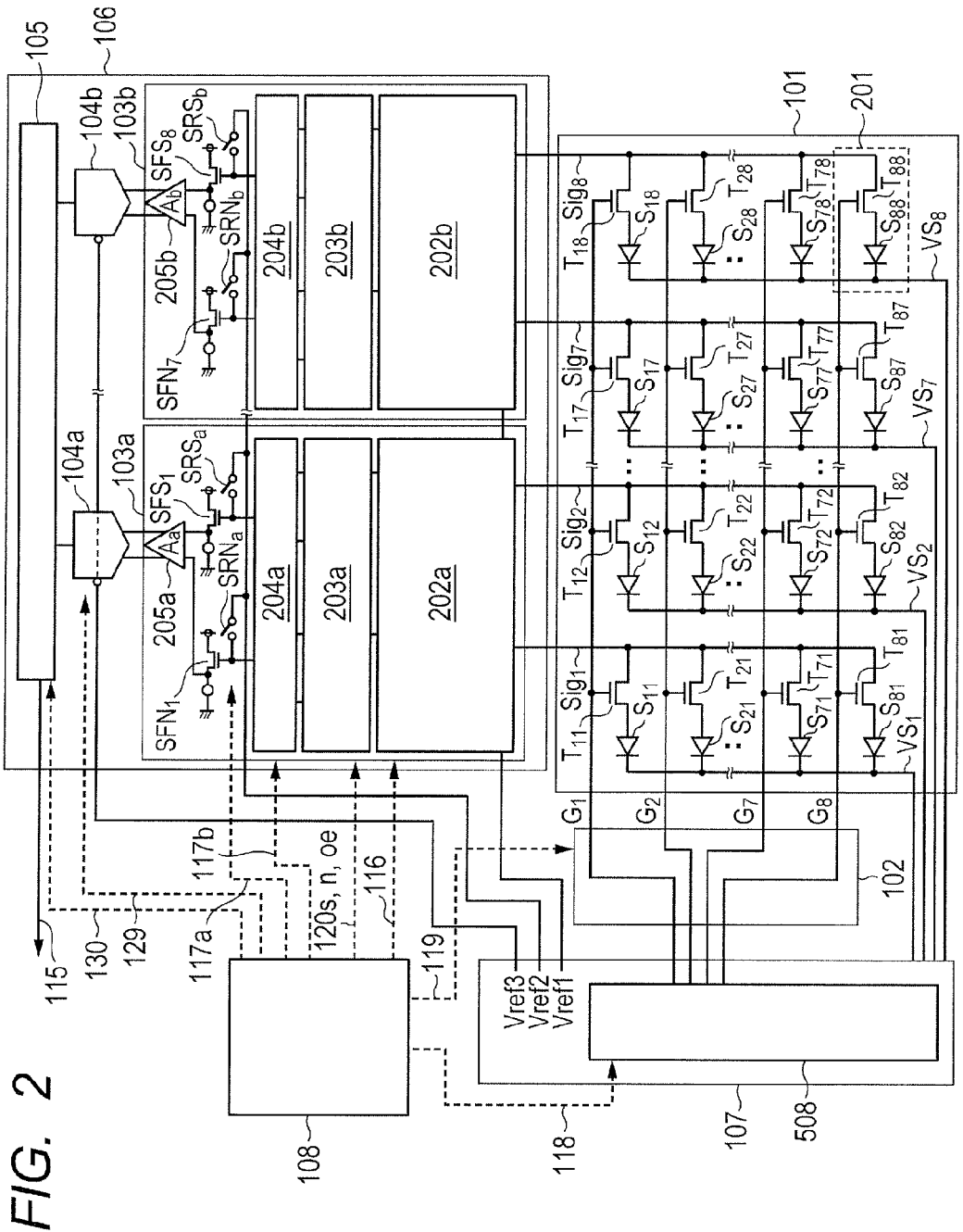
FIG. 2 is a view of an imaging apparatus according to the first embodiment.

FIG. 2 is a view that illustrates a configuration example of the imaging apparatus 100. Note that elements in FIG. 2 having the same configuration as that described using FIG. 1 are assigned the same reference numerals, and detailed descriptions thereof are omitted. The detection unit 101 has a plurality of pixels 201 that are arranged in a matrix shape. In FIG. 2, 8×8 pixels are arranged over 8 rows and 8 columns. Each of the plurality of pixels 201 includes a conversion element S that converts radiation or light into an electric charge, and a switching element T that outputs an electrical signal that is based on the electric charge of the conversion element S to a signal line Sig. The plurality of pixels 201 are arranged in a two-dimensional matrix shape. A photoelectric conversion element such as a PIN-type photodiode or an MIS-type photodiode that is provided on an insulating substrate such as a glass substrate and that includes amorphous silicon as the main material can be used as the conversion element S that converts light into an electric charge. An indirect-type conversion element having a wavelength converter that is provided on the side on which radiation is incident of the above-described photoelectric conversion element and that converts radiation into light falling within the band of wavelengths that can be sensed by the photoelectric conversion element, or a direct-type conversion element that directly converts radiation into an electric charge can be used as the conversion element that converts radiation into an electric charge. A transistor having a control terminal and two main terminals can be used as the switching element T, and in the case of a pixel having the photoelectric conversion element S provided on an insulating substrate, a thin film transistor (TFT) can be used. One of the electrodes of the conversion element S is electrically connected to one of the two main terminals of the switching element T, and the other electrode is electrically connected to sensor bias lines $VS_1$ to $VS_8$ via a common line. A sensor bias Vs is supplied to the sensor bias lines $VS_1$ to $VS_8$, and the sensor bias lines $VS_1$ to $VS_8$ supply the sensor bias Vs to the conversion elements S. Switching elements T of a plurality of pixels in the row direction, for example, switching elements $T_{11}$ to $T_{18}$, have control terminals that are commonly electrically connected to a drive line G1 of the first row. Drive signals for controlling the conductive state of the switching elements T are applied from the drive circuit 102 via drive lines G on in row units. In the switching elements T of the plurality of pixels in the column direction, for example, switching elements $T_{11}$ to $T_{81}$, the other main terminals thereof are electrically connected to a signal line $Sig_1$ of the first column. Electrical signals corresponding to the electric charge of the conversion elements S are output to the read circuit 103 via signal lines Sig during a period in which the switching elements T are in a conductive state.

According to the present embodiment, the drive lines $G_1$ to $G_8$ that extend in the horizontal direction and the sensor bias lines $VS_1$ to $VS_8$ that extend in the vertical direction are connected to the AEC monitor unit 508. The AEC monitor unit 508 monitors (detects) currents that flow in the drive lines $G_1$ to $G_8$ and the sensor bias lines $VS_1$ to $VS_8$ during X-ray irradiation. A plurality of signal lines $Sig_1$ to $Sig_8$ arranged in the column direction transmit the electrical signals output from the plurality of pixels 201 of the detection unit 101 to the read circuit 103 in parallel. According to the present embodiment, the detection unit 101 is divided into the first pixel group 101a and the second pixel group 101b that each includes four pixel columns. Analog electrical signals that were output from the first pixel group 101a are read in parallel by the corresponding first read circuit 103a in the read circuit 103, and analog electrical signals that output from the second pixel group 101b are read in parallel by the second read circuit 103b.

Figure 3:
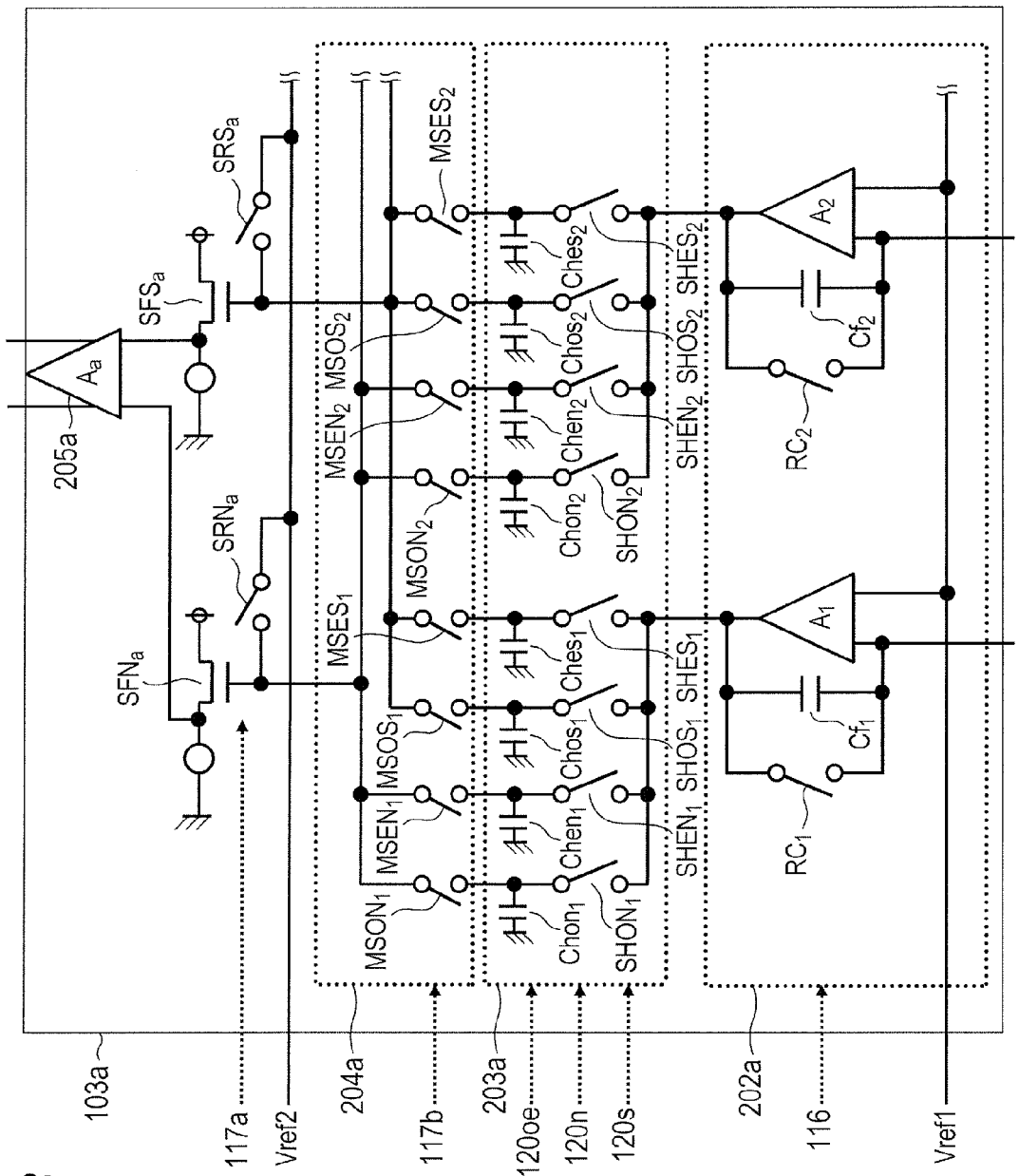
FIG. 3 is a view of a first read circuit according to the first embodiment.

FIG. 3 is a view that illustrates a configuration example of the first read circuit 103a. Although the following description takes the configuration of the first read circuit 103a as an example, the configuration of the second read circuit 103b is the same as that of the first read circuit 103a. The first read circuit 103a includes a first amplification circuit unit 202a configured to amplify the electrical signals that are output in parallel from the first pixel group 101a, and a first sample and hold circuit unit 203a that samples and holds electrical signals from the first amplification circuit unit 202a. The second read circuit 103b similarly includes a second amplification circuit unit 202b and a second sample and hold circuit unit 203b. The first and second amplification circuit units 202a and 202b each includes an operational amplifier A configured to amplify and output the read electrical signal, an integration capacitor group Cf and a reset switch RC configured to reset the integration capacitors Cf, and are provided in correspondence with the respective signal lines Sig. An electrical signal of the signal line Sig is input to an inverting input terminal of the operational amplifier A, and an amplified electrical signal is output from an output terminal of the operational amplifier A. The reference voltage Vref1 is input to the non-inverting input terminal of the operational amplifier A. The first and second sample and hold circuit units 203a and 203b include sampling switches SHON, SHEN, SHOS and SHES, and sampling capacitors Chon, Chen, Chos and Ches, and are provided in correspondence with the respective amplification circuit units 202a and 202b. The first read circuit 103a includes a first multiplexer 204a that sequentially outputs electrical signals read in parallel from the first sample and hold circuit unit 203a and that outputs the electrical signals as serial image signals. Similarly, the second read circuit 103b includes a second multiplexer 204b that sequentially outputs electrical signals read in parallel from the second sample and hold circuit unit 203b and that outputs the electrical signals as serial image signals. The first multiplexer 204a includes switches MSON, MSEN, MSOS and MSES that correspond to the sampling capacitors Chon, Chen, Chos and Ches, and converts parallel signals to serial signals by sequentially selecting the respective switches. The first read circuit 103a also includes output buffer circuits SFN and SFS that perform impedance conversion on the output signals of the first multiplexer 204a, switches SRN and SRS, and a first variable amplifier 205a. In FIG. 2, the A/D converter 104a converts the output signals of the first variable amplifier 205a from analog signals to digital signals, and outputs image data to the signal processing circuit 105.

Figure 4:
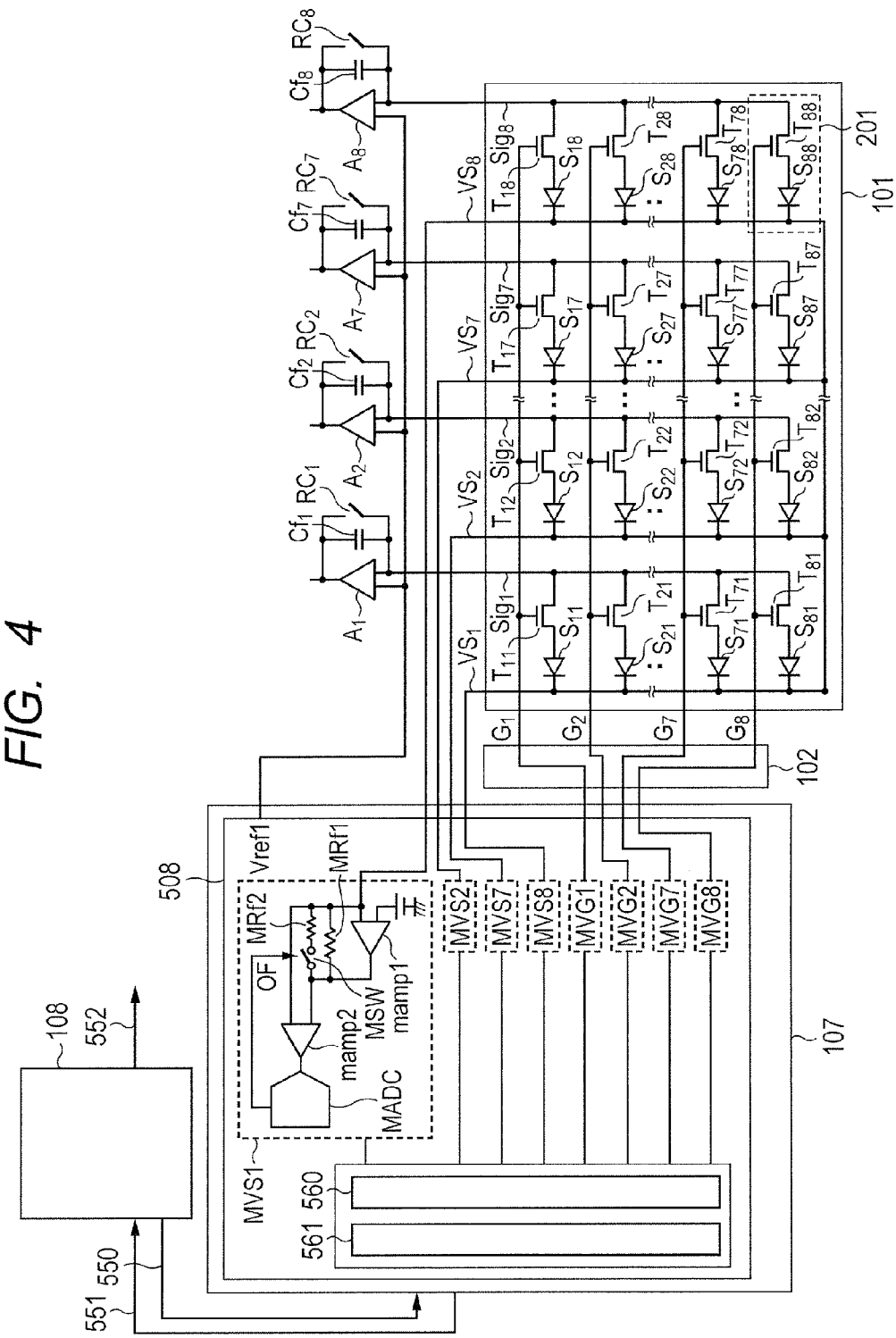
FIG. 4 is a view of the imaging apparatus according to the first embodiment.

FIG. 4 is a view that illustrates a configuration example of the imaging apparatus 100 according to the present invention. Note that elements in FIG. 4 having the same configuration as that described using FIG. 2 are assigned the same reference numerals, and detailed descriptions thereof are omitted. The AEC monitor unit 508 includes sensor bias current monitor circuit units $MVS_1$ to $MVS_8$, drive line current monitor circuit units $MVG_1$ to $MVG_8$, filter unit 560 and arithmetic unit 561. The sensor bias current monitor circuit units $MVS_1$ to $MVS_8$ monitor currents flowing in the sensor bias lines $VS_1$ to $VS_8$. The drive line current monitor circuit units $MVG_1$ to $MVG_8$ monitor currents flowing in the drive lines $G_1$ to $G_8$. The filter unit 560 performs filter processing on monitor output results of the sensor bias current monitor circuit units $MVS_1$ to $MVS_8$ and the drive line current monitor circuit units $MVG_1$ to $MVG_8$. The arithmetic unit 561 performs back-projection processing on output results of the filter unit 560, calculates a value of a region of interest, and if the value of the region of interest exceeds a previously set threshold value, outputs the stop signal 551 to the control unit 108 to stop X-ray irradiation. Further, region of interest information and threshold value information are output to the AEC monitor unit 508 from the control unit 108 by means of a monitor condition signal 550.

The sensor bias current monitor circuit units $MVS_1$ to $MVS_8$ include a transimpedance amplifier mamp1, feedback resistances MRF1 and MRF2, a switch MSW, an instrumentation amplifier mamp2 and an analog-to-digital converter MADC. Similarly, the drive line current monitor circuit units $MVG_1$ to $MVG_8$ include the transimpedance amplifier mamp1, the feedback resistances MRF1 and MRF2, the switch MSW, the instrumentation amplifier mamp2 and the analog-to-digital converter MADC. The transimpedance amplifier mamp1 converts a current flowing in the sensor bias lines $VS_1$ to $VS_B$ or the drive lines $G_1$ to $G_8$ into a voltage. The feedback resistances MRF1 and MRF2 set a conversion gain when converting a current into a voltage. The instrumentation amplifier mamp2 further multiplies the voltage obtained by conversion at the transimpedance amplifier mamp1 by the gain. The analog-to-digital converter MADC converts the voltage value from the instrumentation amplifier mamp2 from an analog value to a digital value. Monitoring to realize the AEC function cannot be correctly performed unless a signal is input that is within an input range of the analog-to-digital converter MADC. Therefore, a gain changeover switch MSW for lowering the current-voltage conversion gain when the analog-to-digital converter MADC has overflowed is provided. Thus, AGC (automatic gain control) is realized that changes over the switch MSW by means of an overflow signal OF.

FIG. 5 is a flowchart illustrating operations of the imaging apparatus according to the present invention. FIGS. 6A to 6D, FIGS. 7A to 7C and FIG. 8 are views that illustrate methods of processing monitor output results. Operations of the first embodiment will now be described referring to the flowchart shown in FIG. 5. In step S301, a monitoring position (region of interest) of the AEC is designated by a technician before photographing. The X-ray control apparatus 502 performs control of the X-ray generating apparatus 501 so that the amount of X-rays at the designated monitoring position becomes the optimal amount. Designation of the monitoring position can be performed by a technician, or the monitoring position can be automatically decided by designating a photographing site. Information regarding the designated monitoring position is output to the AEC monitor unit 508 from the control unit 108 by means of the monitor condition signal 550.

In step S302, photographing is started. In step S303, a voltage is supplied to the sensor bias lines $VS_1$ to $VS_8$ in the detection unit 101, and the imaging apparatus 100 performs idling (K). In the idling (K), the drive lines $G_1$ to $G_8$ are actuated in sequential order, the switching elements T are turned on in row units, and resetting of a dark current that flows in the conversion elements S is performed. Next, in step S304, the exposure button 503 is pushed. Thereafter, in step S305, the reset operation is performed as far as the last drive line $G_8$, and the imaging apparatus 100 transitions to an accumulation operation (W). Next, in step S306, the AEC monitor unit 508 starts to monitor the currents flowing in the sensor bias lines $VS_1$ to $VS_8$ and the drive lines $G_1$ to $G_8$. When X-rays (light) are irradiated onto the conversion elements S, electrons and positive holes are generated in the conversion elements S, and because the switching elements T are turned off during the period of the accumulation operation (W), most of the generated electrons and positive holes do not flow to an external circuit and are accumulated in the conversion elements S. A part of a current that depends on a parasitic capacitance of the switching elements T flows to the sensor bias lines $VS_1$ to $VS_8$ and the drive lines $G_1$ to $G_8$, and the amount of X-rays irradiated during the accumulation operation (W) is monitored by measuring the current.

Figure 6A:
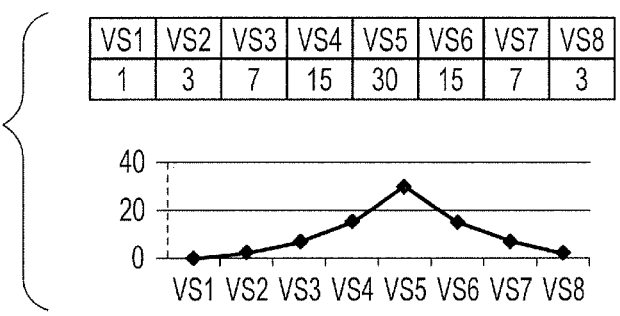
FIGS. 6A, 6B, 6C and 6D are views illustrating a processing method of the imaging system according to the first embodiment.
Figure 6B:
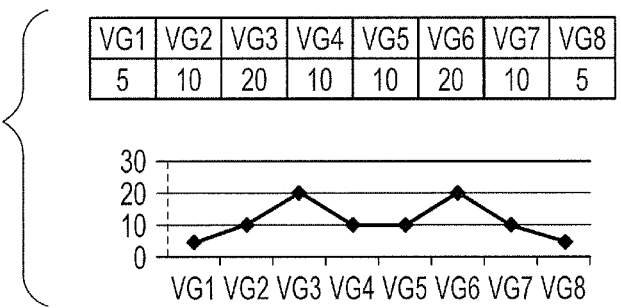

A current of an amount in proportion to the amount of X-rays that were irradiated onto the conversion elements $S_{11}$ to $S_{81}$ connected to the sensor bias line $VS_1$ flows in the sensor bias lines $VS_1$, and a current of an amount in proportion to the amount of X-rays irradiated onto the conversion elements $S_{11}$ to $S_{18}$ flows in the drive line $G_1$. The currents that flowed through the aforementioned lines are converted into digital values via the transimpedance amplifier mamp1, the instrumentation amplifier mamp2 and the analog-to-digital converter MADC. FIG. 6A is a view that represents currents that flow in the sensor bias lines $VS_1$ to $VS_8$, and FIG. 6B is a view that represents currents that flow in the drive lines $G_1$ to $G_8$. In step S307, the sensor bias current monitor circuit units $MVS_1$ to $MVS_8$ and the drive line current monitor circuit units $MVG_1$ to $MVG_8$ output the digital values of the currents that flow in the sensor bias lines $VS_1$ to $VS_8$ and the drive line $G_1$ to $G_8$, respectively.

Figure 6C:
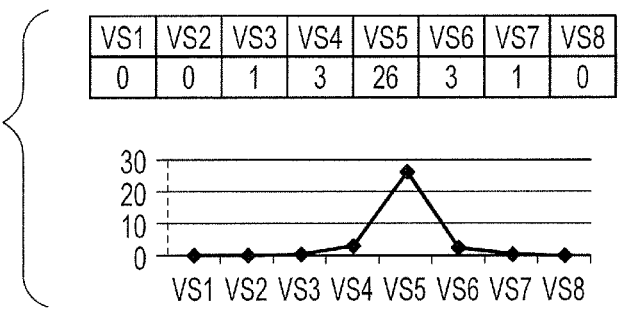
Figure 6D:
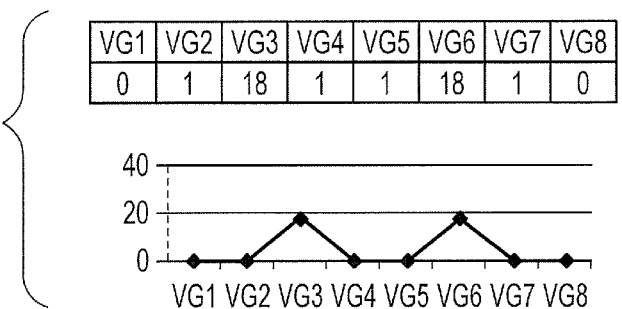

Next, in step S308, the filter unit 560 performs filter processing on the digital values output from the sensor bias current monitor circuit units $MVS_1$ to $MVS_8$ and the drive line current monitor circuit units $MVG_1$ to $MVG_8$. Because the digital values output from the sensor bias current monitor circuit units $MVS_1$ to $MVS_8$ and the drive line current monitor circuit units $MVG_1$ to $MVG_8$ includes a large amount of low-frequency noise components, the low-frequency components are removed via a high-pass filter of the filter unit 560. Values output from the filter unit 560 are illustrated in FIGS. 6C and 6D. FIG. 6C is a view that represents currents of the sensor bias lines $VS_1$ to $VS_8$, and FIG. 6D is a view that represents currents of the drive lines $G_1$ to $G_8$.

Figures 7A, 7B, 7C:
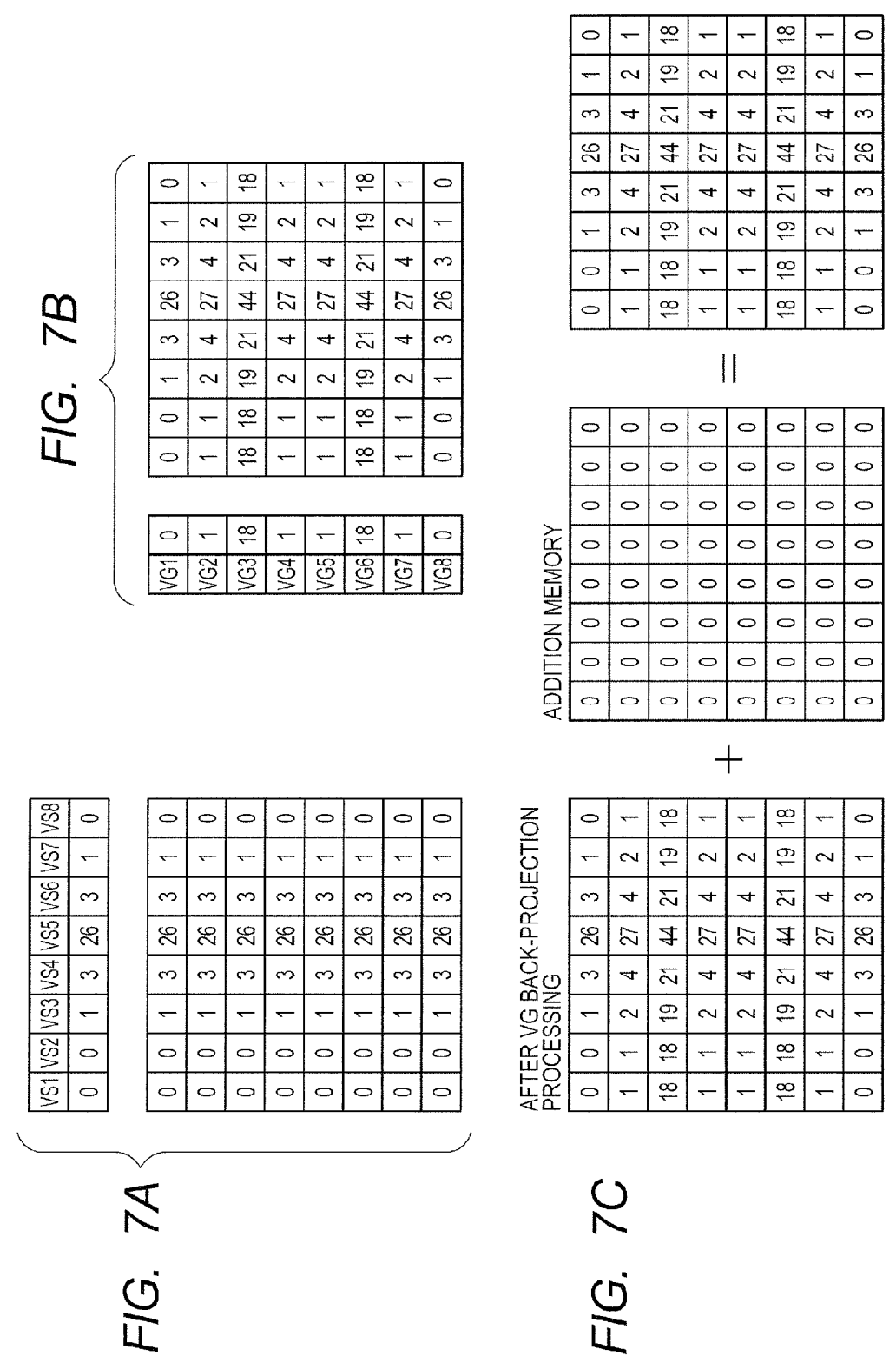

Next, in step S309, in order to convert the output values of the filter unit 560 into two-dimensional data, the arithmetic unit 561 performs back-projection processing with respect to the sensor bias lines $VS_1$ to $VS_8$ that extend in the vertical direction. FIG. 7A is a view that illustrates back-projection processing with respect to the sensor bias lines $VS_1$ to $VS_8$, in which one-dimensional output results output from the filter unit 560 are back-projected onto a two-dimensional memory. When performing the back-projection processing, since the digital values output from the sensor bias current monitor circuit units $MVS_1$ to $MVS_8$ and the drive line current monitor circuit units $MVG_1$ to $MVG_8$ are values obtained by integrating the values for one column or one row, values obtained by dividing the digital values by the number of rows or the number of columns, respectively, are subjected to the back-projection processing.

Next, in step S310, as shown in FIG. 7B, the arithmetic unit 561 performs back-projection processing with respect to the drive lines $G_1$ to $G_8$ that extend in the horizontal direction. Thereafter, in step S311, the arithmetic unit 561 adds the back-projection results for the drive lines $G_1$ to $G_8$ that extend in the vertical direction to the results of the back-projection processing (FIG. 7A) for the sensor bias lines $VS_1$ to $VS_8$ that extend in the vertical direction. The filter processing and back-projection processing are performed by a similar method to reconstruction processing that is performed by a CT apparatus. By performing back-projection processing for the sensor bias lines $VS_1$ to $VS_8$ that extend in the vertical direction and back-projection processing for the drive lines $G_1$ to $G_8$ that extend in the horizontal direction, a two-dimensional distribution of X-rays transmitted through the subject can be obtained. That is, the sensor bias current monitor circuit units $MVS_1$ to $MVS_8$ and the drive line current monitor circuit units $MVG_1$ to $MVG_8$ monitor currents that flow in the sensor bias lines $VS_1$ to $VS_8$ and the drive lines $G_1$ to $G_8$ that extend in two different directions that are connected to the plurality of pixels 201. The arithmetic unit 561 calculates the two-dimensional distribution by performing back-projection processing with respect to the currents flowing in the sensor bias lines $VS_1$ to $VS_8$ and the drive lines $G_1$ to $G_8$ that extend in the two different directions. Next, since it is necessary to calculate an integrated value of the X-ray amounts at the monitoring position (region of interest) to realize the AEC function, as shown in FIG. 7C, the arithmetic unit 561 adds the back-projection processing results shown in FIG. 7B to the addition memory.

Next, in step S312, as shown in FIG. 8, the arithmetic unit 561 performs subject correction processing by multiplying the values of the addition memory after the addition processing as shown in FIG. 7C by subject correction coefficients. Depending on the site that is photographed, a large amount of X-rays is irradiated at a part of the detector 101 and the output of a corresponding column or row increases, and it is not possible to accurately read the value of a portion at which a small amount of X-rays was irradiated in the same column. Therefore, by calculating subject correction coefficients in advance in accordance with the photographing site and multiplying by the subject correction coefficients, the amount of X-rays of a region of interest can be monitored with a high degree of accuracy. FIG. 8 illustrates an example with respect to photographing of the chest. When photographing the chest, the output increases because X-ray absorption does not occur at portions at the sides of the torso (regions of row 5 to row 8 of column 1 and column 8 in FIG. 8). However, since current that is the total for one row flows in the drive lines $G_1$ to $G_8$, it appears as if one row was averaged. Therefore, when back-projection processing is performed, a value for a place at which the output is a large value decreases and a value for a place at which the output is a small value increases. Since the relationship between the sizes of outputs at a region depends on the photographing site, it is possible to calculate subject correction coefficients in advance and perform correction.

Next, in step S313, the arithmetic unit 561 determines whether or not a value after subject correction at a previously set monitoring position exceeds a threshold value, and if the value does not exceed the threshold value, the arithmetic unit 561 returns to step S307 to continue the monitoring. If the aforementioned value exceeds the threshold value, in step S314, the arithmetic unit 561 outputs the stop signal 551 for stopping the X-ray irradiation to the control unit 108, and the control unit 108 stops the X-ray irradiation (radiation irradiation) of the X-ray generating apparatus 501 through the X-ray control apparatus 502. With respect to the determination method, the user may designate a monitoring position in advance, or a monitoring position may be decided according to the photographing site or the like. Further, with respect to the size of the monitoring position, any one of an average value, a maximum value and a minimum value of a single region (for example, row 3, column 3) or a plurality of regions (for example, rows 3 to 5, columns 3 to 6) may be compared with the threshold value. Further, methods are available which have a single threshold value, or have a plurality of threshold values that differ by region in a matrix shape, and which stop the X-ray irradiation if any one value exceeds a threshold value, or if all values exceed a threshold value, or if half or more of the values exceed a threshold value. After the X-ray irradiation has been stopped, in step S315, the imaging apparatus 100 starts a read operation for a subject image that is to be used for diagnosis.

By monitoring currents flowing in the sensor bias lines $VS_1$ to $VS_8$ and the drive lines $G_1$ to $G_8$ and performing back-projection processing in this manner, it is possible to determine the amount of X-rays at a region of interest that were transmitted through a subject. The AEC function can be realized by controlling the X-ray generating apparatus 501 so that the amount of X-rays at the region of interest becomes the optimal amount based on the determined amount of X-rays.

Second Embodiment

Figure 9:
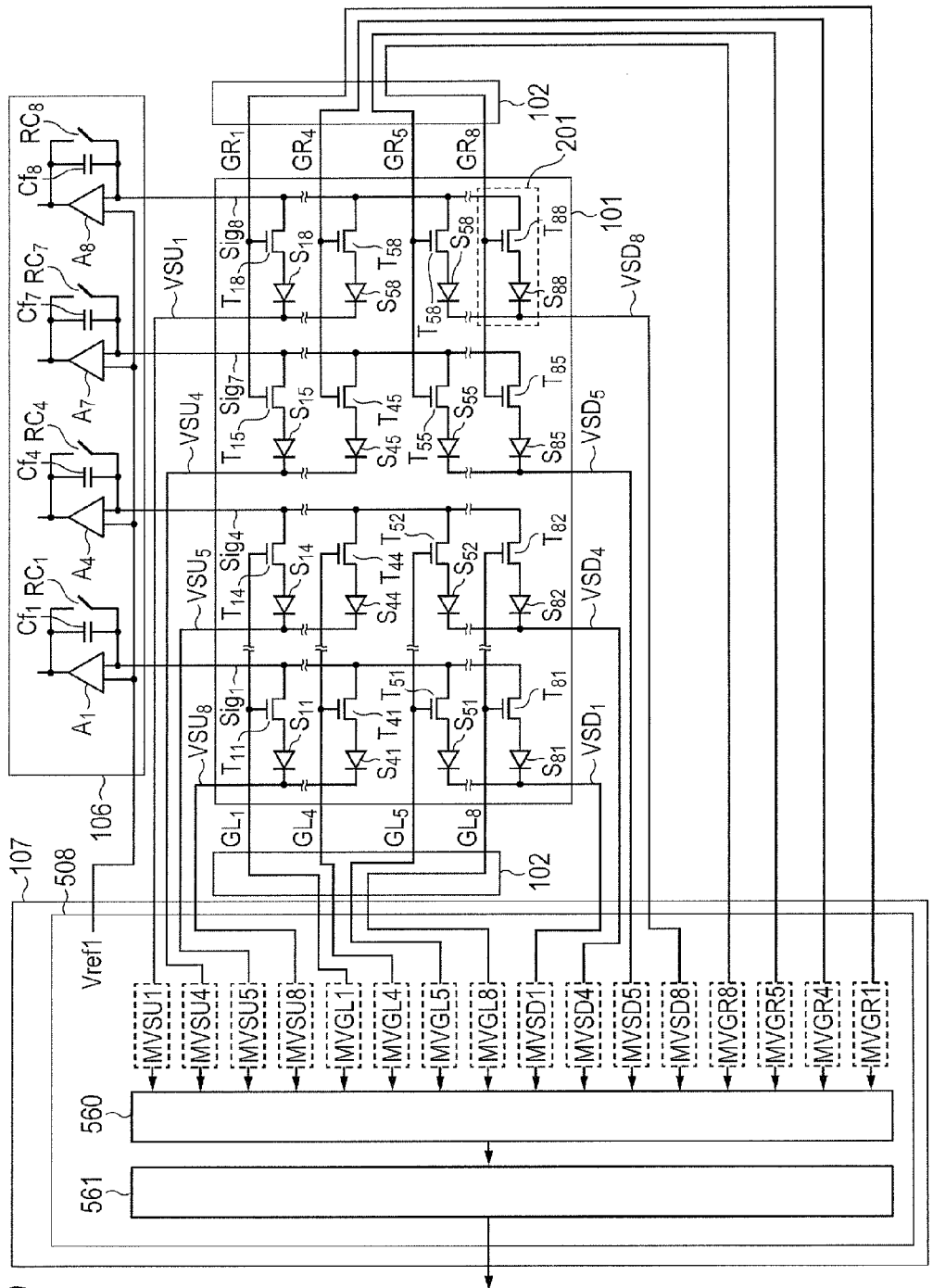
FIG. 9 is a view of an imaging apparatus according to a second embodiment.

FIG. 9 is a view that illustrates a configuration example of the imaging apparatus 100 according to a second embodiment of the present invention. Note that elements in FIG. 9 having the same configuration as that described in the first embodiment are assigned the same reference numerals, and detailed descriptions thereof are omitted. In the first embodiment, the sensor bias lines $VS_1$ to $VS_8$ were wired commonly to a single column and the drive lines $G_1$ to $G_8$ were wired commonly to a single row. When a large amount of X-rays is irradiated at a part of the detector 101 and the output of a corresponding column or row increases, and it is not possible to accurately read the value of a portion at which a small amount of X-rays was irradiated in the same column. Therefore, according to the second embodiment, the sensor bias lines $VS_1$ to $VS_8$ are divided into two groups on the upper and lower sides, namely, sensor bias lines $VSU_1$ to $VSU_8$ and $VSD_1$ to $VSD_8$, and the drive lines $G_1$ to $G_8$ are divided into two groups on the left and right sides, namely, drive lines $GR_1$ to $GR_8$ and $GL_1$ to $GL_8$. Thus, according to the present embodiment, the detector 101 is divided into a total of four blocks. Consequently, even if a large amount of X-rays is irradiated at one part of the detector 101, it is possible to accurately monitor the X-rays at another block. The drive circuit 102 supplies a drive signal to the drive lines $GR_1$ to $GR_8$ and $GL_1$ to $GL_8$. The sensor bias current monitor circuit units $MVSU_1$ to $MVSU_8$ monitor currents flowing in the sensor bias lines $VSU_1$ to $VSU_8$ and output the monitoring results to the filter unit 560. The sensor bias current monitor circuit units $MVSD_1$ to $MVSD_8$ monitor currents flowing in the sensor bias lines $VSD_1$ to $VSD_8$ and output the monitoring results to the filter unit 560. The drive line current monitor circuit units $MVGL_1$ to $MVGL_8$ monitor currents flowing in the drive lines $GL_1$ to $GL_8$ and output the monitoring results to the filter unit 560. The drive line current monitor circuit units $MVGR_1$ to $MVGR_8$ monitor currents flowing in the drive lines $GR_1$ to $GR_8$ and output the monitoring results to the filter unit 560.

As described above, the current monitor circuit units may be configured to monitor currents in each region into which the plurality of pixels 201 are divided with respect to at least one line among lines that extend in two or more different directions.

Third Embodiment

Figure 10:
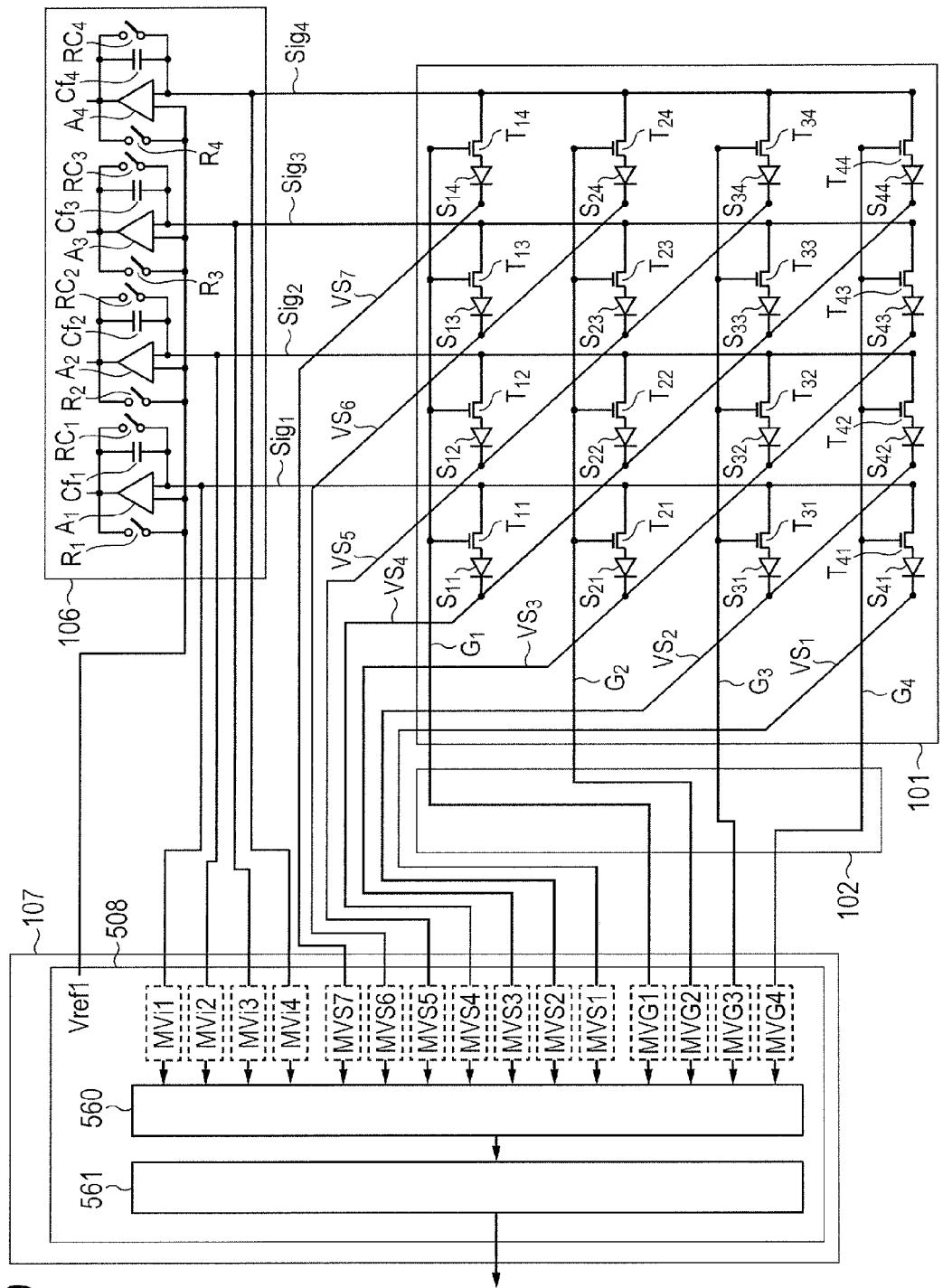
FIG. 10 is a view of an imaging apparatus according to a third embodiment.

FIG. 10 is a view that illustrates a configuration example of the imaging apparatus 100 according to a third embodiment of the present invention. Note that elements in FIG. 10 that have the same configuration as that described in the first embodiment are assigned the same reference numerals, and detailed descriptions thereof are omitted. In the first embodiment, because the arrangement of the lines is such that the sensor bias lines $VS_1$ to $VS_8$ and the drive lines $G_1$ to $G_8$ are orthogonal to each other, back-projection processing is performed from two directions. According to the third embodiment, the sensor bias lines $VS_1$ to $VS_7$ are wired in a diagonal direction. The sensor bias current monitor circuit units $MVS_1$ to $MVS_7$ monitor currents that flow in the sensor bias lines $VS_1$ to $VSD_7$ that extend in the diagonal direction, and output the monitoring results to the filter unit 560. The drive line current monitor circuit units $MVG_1$ to $MVG_4$ monitor currents that flow in the drive lines $G_1$ to $G_4$ that extend in the horizontal direction, and output the monitoring results to the filter unit 560.

Figure 11:
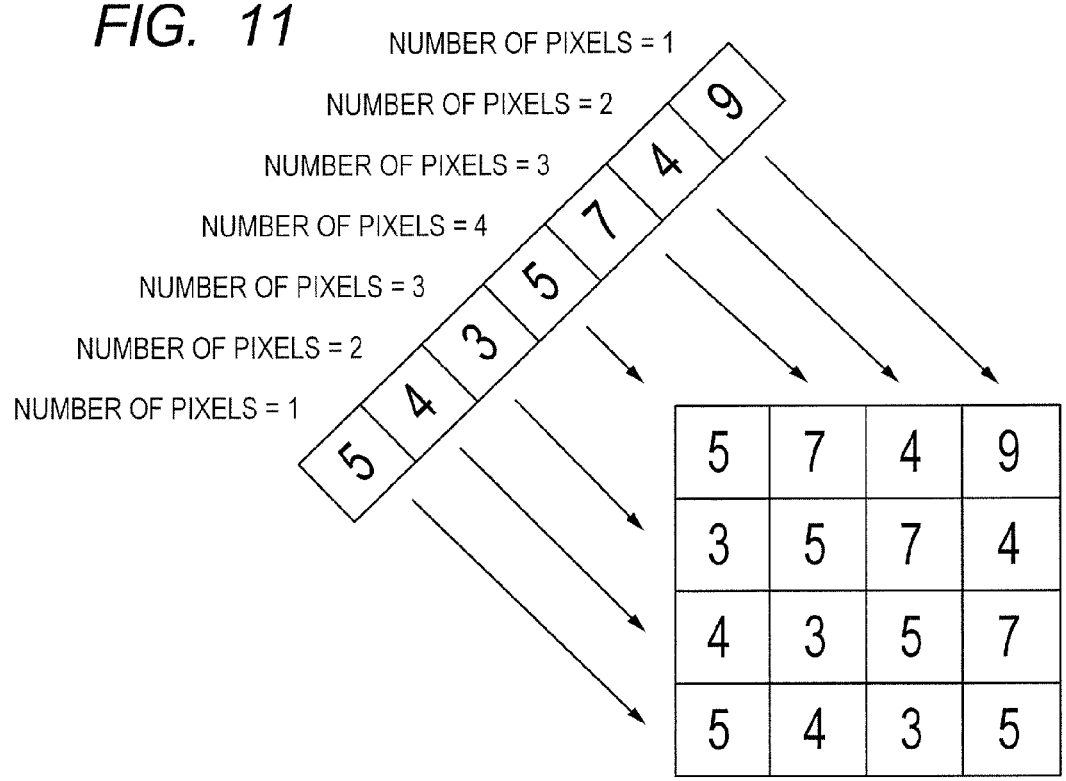
FIG. 11 is a view that illustrates processing of an arithmetic unit according to the third embodiment.

In addition, switches $R_1$ to $R_4$ are connected between a non-inverting input terminal and an output terminal of operational amplifiers $A_1$ to $A_4$, respectively. Signal line current monitor circuit units MVi1 to MVi4 have the same configuration as the above described sensor bias current monitor circuit units $MVS_1$ to $MVS_7$, and monitor currents flowing in signal lines $Sig_1$ to $Sig_4$ that extend in the vertical direction, and output the monitoring results to the filter unit 560. Since the sensor bias current monitor circuit units $MVS_1$ to $MVS_7$, the drive line current monitor circuit units $MVG_1$ to $MVG_4$ and the signal line current monitor circuit units MVi1 to MVi4 monitor currents, the arithmetic unit 561 performs back-projection processing for lines in three different directions. When performing back-projection processing, the greater the number of directions for which the back-projection processing is performed, the greater the accuracy with which a two-dimensional distribution can be determined. Further, as shown in FIG. 11, although back-projection processing is also performed in the diagonal direction, since the number of pixels for which results are integrated differs depending on the lines, it is necessary to divide the respective results by the number of pixels whose results are integrated for each line.

Note that, the current monitor circuit units may be configured to monitor currents that flow in lines extending in two or more different directions among the signal lines $Sig_1$ to $Sig_4$, the sensor bias lines $VS_1$ to $VS_7$ and the drive lines $G_1$ to $G_8$. In such case, the arithmetic unit 561 calculates the two-dimensional distribution by performing back-projection processing on currents flowing in lines extending in two or more different directions that are monitored by the current monitor circuit units.

Fourth Embodiment

Figure 12:
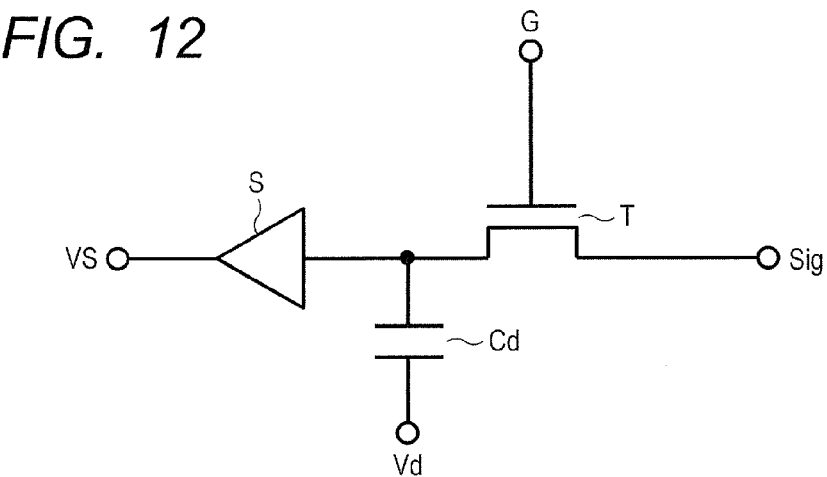
FIG. 12 is a view of a pixel according to a fourth embodiment.

FIG. 12 is a view that illustrates a configuration example of a pixel 201 (FIG. 2) according to a fourth embodiment of the present invention. Note that elements in FIG. 12 having the same configuration as that described in the third embodiment are assigned the same reference numerals, and detailed descriptions thereof are omitted. As shown in FIG. 12, a dummy line Vd is connected to an interconnection point between the conversion element S and the switching element T via a capacitor Cd. It is thereby possible to extract a current generated by irradiated X-rays to an external circuit through the dummy line Vd.

Figure 13:
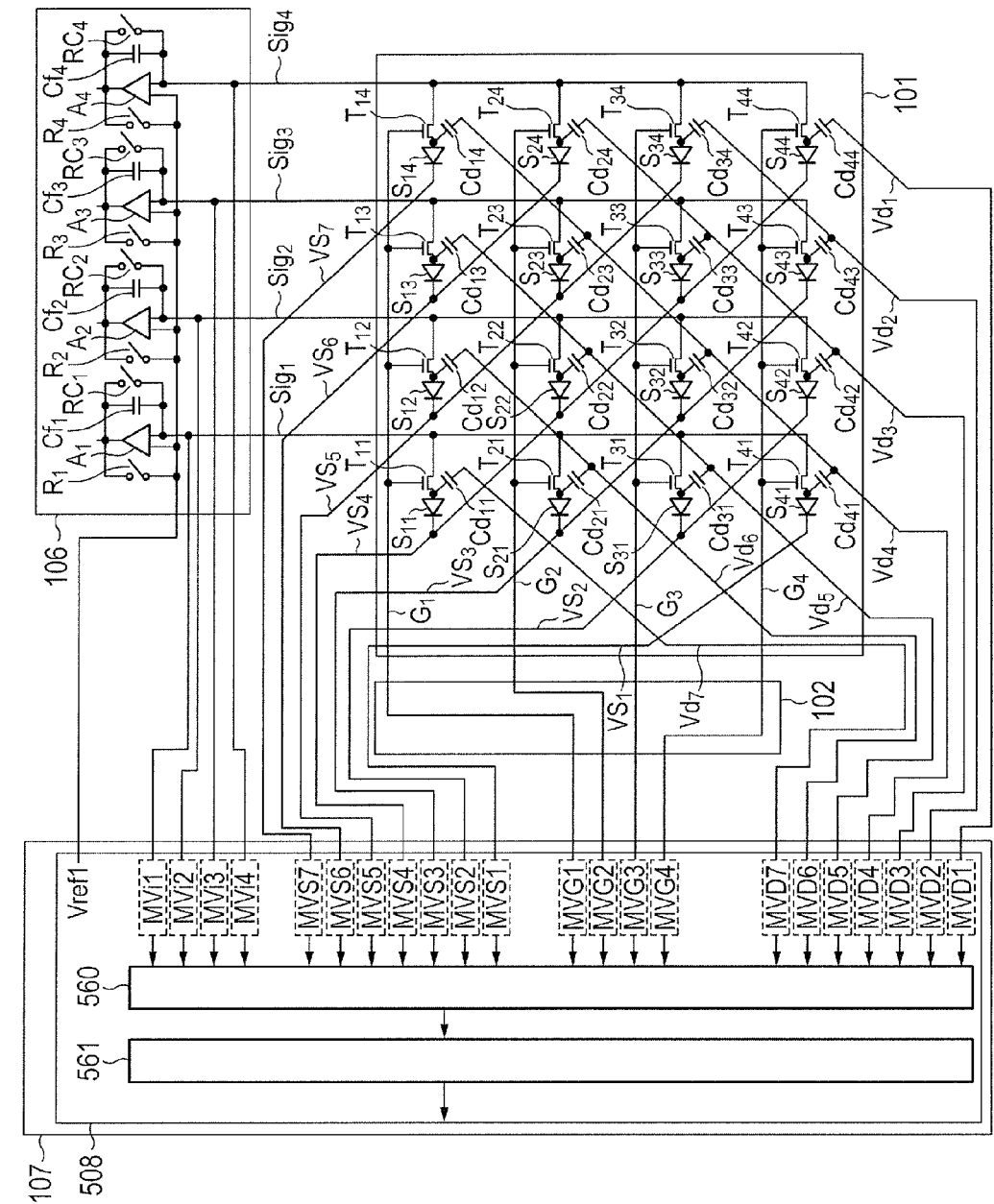
FIG. 13 is a view of an imaging apparatus according to the fourth embodiment.

FIG. 13 is a view that illustrates a configuration example of an imaging apparatus according to the present invention, which illustrates a method of wiring the dummy lines Vd inside the detector 101. Dummy lines $Vd_1$ to $Vd_7$ are arranged so as to be orthogonal to the sensor bias lines VS' to $VS_7$, and are connected in the diagonal direction to the respective capacitors Cd of the pixels 201 in a matrix shape. The dummy line current monitor circuit units $MVD_1$ to $MVD_7$ have the same configuration as the above described sensor bias current monitor circuit units $MVS_1$ to $MVS_7$ and the drive line current monitor circuit units $MVG_1$ to $MVG_4$, and monitor currents that flow in the dummy lines $VS_1$ to $VS_7$, and output the monitoring results to the filter unit 560. The sensor bias current monitor circuit units $MVS_1$ to $MVS_7$, the drive line current monitor circuit units $MVG_1$ to $MVG_4$, the signal line current monitor circuit units MVi1 to MVi4 and the dummy line current monitor circuit units $MVD_1$ to $MVD_7$ monitor currents. Consequently, the arithmetic unit 561 can perform back-projection processing with respect to lines in four different directions, and it is possible to determine the two-dimensional distribution with greater accuracy. In addition, similarly to the second embodiment, the two-dimensional distribution can be determined with further accuracy by dividing the detector 101 into blocks and leading out lines from four directions.

Note that the current monitor circuit units may be configured to monitor currents that flow in lines extending in two or more different directions among the signal lines $Sig_1$ to $Sig_4$, the sensor bias lines $VS_1$ to $VS_7$, the drive lines $G_1$ to $G_8$ and the dummy lines $Vd_1$ to $Vd_7$. In that case, the arithmetic unit 561 calculates the two-dimensional distribution by performing back-projection processing on currents that flow in lines extending in two or more different directions that are monitored by the current monitor circuit units.

Fifth Embodiment

Figure 14:
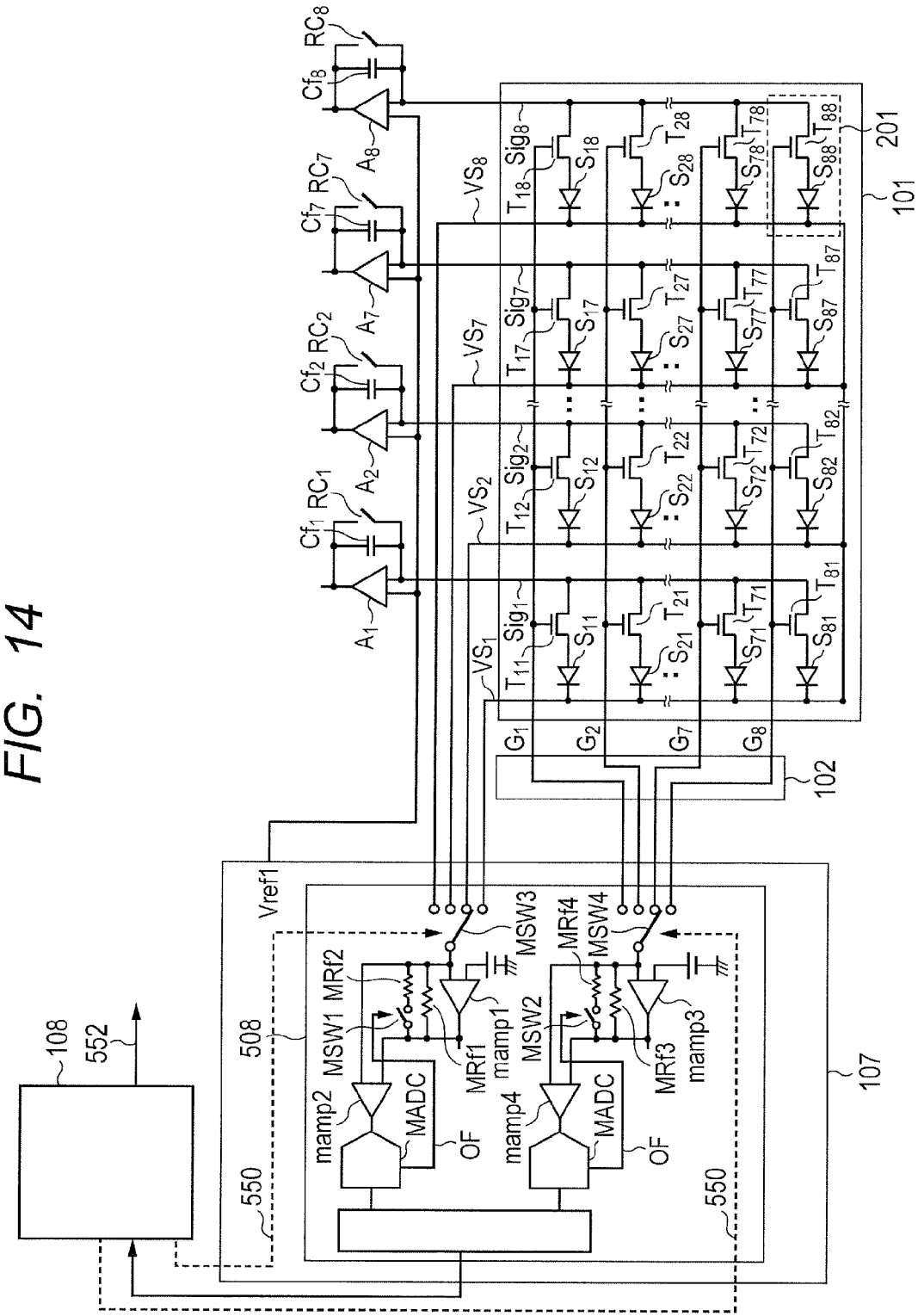
FIG. 14 is a view of an imaging system according to a fifth embodiment.

FIG. 14 is a view that illustrates a configuration example of an imaging apparatus according to a fifth embodiment of the present invention. Note that elements in FIG. 14 having the same configuration as that described in the first embodiment are assigned the same reference numerals, and detailed descriptions thereof are omitted. Although according to the first embodiment the sensor bias lines VS and the drive lines G over the entire surface of the detector 101 are monitored, according to the fifth embodiment only a current that flows in the sensor bias lines VS and a current that flows in the drive lines G at a monitoring position are measured. A column selection switch MSW3 and a row selection switch MSW4 are set to a monitoring position by means of the monitor condition signal 550 that is output from the control unit 108 to the AEC monitor unit 508, and only the monitoring position is measured. The column selection switch MSW3 selectively connects the sensor bias current monitor circuit unit MVS to the sensor bias line VS of the column at the monitoring position, and the row selection switch MSW4 selectively connects the drive line current monitor circuit unit MVG to the drive line G of the row at the monitoring position. By adopting this configuration, it is possible to reduce the scale of the circuit, decrease the electrical power consumption, and prevent an increase in the size of the apparatus.

It is to be understood that the foregoing first to fifth embodiments are intended to illustrate specific examples for implementing the present invention, and are not intended to limit the technical scope of the present invention. That is, the present invention can be implemented in various forms without departing from the technical concept or the principal features thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-288451, filed Dec. 28, 2012, which is hereby incorporated by reference herein in its entirety.

What is claimed is:

1. A radiation imaging apparatus comprising:
a plurality of pixels arranged in a matrix shape for converting x-ray radiation into an electric signal;
a plurality of lines that are connected to the plurality of pixels and that extend in different directions to each other;
a current monitor circuit that monitors currents flowing in the plurality of lines; and
an arithmetic unit that calculates a two-dimensional distribution by performing back-projection processing with respect to the currents flowing in the plurality of lines monitored by the current monitor circuit.

2. The radiation imaging apparatus according to claim 1, wherein each of the plurality of pixels includes a conversion element for converting the x-ray radiation into an electric charge and a switching element that outputs the electrical signal based on the electric charge to a signal line;
the plurality of lines include the signal line, a sensor bias line that supplies a bias to the conversion element, and a drive line for controlling the switching element; and
the current monitor circuit monitors currents that flow in lines extending in two or more different directions among the signal line, the sensor bias line and the drive line.

3. The radiation imaging apparatus according to claim 2, wherein the plurality of lines further include a dummy line connected to the conversion element through a capacitor; and
the current monitor circuit monitors currents that flow in lines extending in two or more different directions among the signal line, the sensor bias line, the drive line and the dummy line.

4. The radiation imaging apparatus according to claim 2, wherein the current monitor circuit monitors currents that flow in lines extending in three different directions that are the signal line, the sensor bias line and the drive line.

5. The radiation imaging apparatus according to claim 3, wherein the current monitor circuit monitors currents that flow in lines extending in four different directions that are the signal line, the sensor bias line, the drive line and the dummy line.

6. The radiation imaging apparatus according to claim 1, wherein the current monitor circuit monitors currents in each region into which the plurality of pixel units are divided.

7. A radiation imaging system comprising:
a radiation imaging apparatus according to claim 1;

a radiation generating apparatus that irradiates x-ray radiation onto the radiation imaging apparatus; and a control apparatus for controlling the radiation generating apparatus, wherein the arithmetic unit outputs a signal for stopping x-ray radiation irradiation of the radiation generating apparatus via the control apparatus based on the calculated two-dimensional distribution.

* * * * *